(12) United States Patent
Decock et al.

(10) Patent No.: US 9,579,671 B2
(45) Date of Patent: Feb. 28, 2017

(54) NOZZLE AND CONTAINER FOR DISPENSING A LIQUID

(71) Applicants: Thierry Decock, Lyons (FR); Guillaume Grevin, L'Isle d'Abeau (FR); Xavier Julia, Villefontaine (FR); Gaëtan Painchaud, Francheville (FR); Thierry Rimlinger, L'Isle d'Abeau (FR)

(72) Inventors: Thierry Decock, Lyons (FR); Guillaume Grevin, L'Isle d'Abeau (FR); Xavier Julia, Villefontaine (FR); Gaëtan Painchaud, Francheville (FR); Thierry Rimlinger, L'Isle d'Abeau (FR)

(73) Assignee: Nemera La Verpillière S.A.S., La Verpilliere (FR)

( * ) Notice: Subject to any disclaimer, the term of this patent is extended or adjusted under 35 U.S.C. 154(b) by 0 days.

(21) Appl. No.: 14/984,247

(22) Filed: Dec. 30, 2015

(65) Prior Publication Data

US 2016/0107180 A1 Apr. 21, 2016

Related U.S. Application Data

(63) Continuation of application No. 13/754,377, filed on Jan. 30, 2013, now Pat. No. 9,238,532, which is a (Continued)

(30) Foreign Application Priority Data

Jul. 30, 2010 (FR) ...................................... 10 56351

(51) Int. Cl.
*B65D 25/40* (2006.01)
*B05B 11/00* (2006.01)
(Continued)

(52) U.S. Cl.
CPC .......... *B05B 11/007* (2013.01); *A61F 9/0008* (2013.01); *B05B 1/02* (2013.01);
(Continued)

(58) Field of Classification Search
CPC ............ B65D 47/2075; B65D 47/2068; B65D 47/2081; B65D 47/2087; B65D 81/24; B65D 47/2018; B65D 47/205; B05B 11/007
(Continued)

(56) References Cited

U.S. PATENT DOCUMENTS

| 1,621,097 A | 3/1927 | Zammataro |
| 2,628,004 A | 2/1953 | Schlicksupp |
| (Continued) | | |

FOREIGN PATENT DOCUMENTS

| CA | 2492255 A1 | 7/2006 |
| WO | 9201625 A1 | 2/1992 |
| WO | 9710160 A1 | 3/1997 |

*Primary Examiner* — Kevin P Shaver
*Assistant Examiner* — Robert Nichols, II
(74) *Attorney, Agent, or Firm* — St Onge Steward Johston and Reens LLC

(57) ABSTRACT

A tip for dispensing liquid for mounting on a container. A valve includes at least two elements that are mobile in relation to one another, each mobile element including a bearing zone against the other mobile element. One of the mobile elements bears anti-microbial material on or in the immediate proximity of a part of its bearing zone forming a blocking barrier and all surfaces of the dispensing tip in contact with the inside are free of anti-microbial material.

19 Claims, 4 Drawing Sheets

Related U.S. Application Data continuation of application No. PCT/FR2011/051765, filed on Jul. 21, 2011.

(51) Int. Cl.
*B65D 47/20* (2006.01)
*B65D 81/24* (2006.01)
*A61F 9/00* (2006.01)
*B05B 1/02* (2006.01)

(52) U.S. Cl.
CPC ...... *B05B 11/0005* (2013.01); *B65D 47/2018* (2013.01); *B65D 47/2087* (2013.01); *B65D 81/24* (2013.01)

(58) Field of Classification Search
USPC ................ 222/491–496, 420, 499, 514, 547; 137/859; 210/321.6
See application file for complete search history.

(56) References Cited

U.S. PATENT DOCUMENTS

| | | |
|---|---|---|
| 3,412,910 A | 11/1968 | Hahn |
| 5,154,325 A | 10/1992 | Ryder et al. |
| 5,310,094 A | 5/1994 | Martinez et al. |
| 6,145,707 A * | 11/2000 | Baudin ............... B05B 11/0021 222/189.09 |
| 6,202,901 B1 | 3/2001 | Gerber et al. |
| 6,974,053 B2 | 12/2005 | Lautre et al. |
| 2005/0173468 A1* | 8/2005 | Matsumoto ........ B65D 47/2081 222/494 |
| 2005/0224520 A1 | 10/2005 | Janssen et al. |
| 2006/0043116 A1 | 3/2006 | Kawashiro et al. |
| 2009/0236374 A1 | 9/2009 | Pardes et al. |
| 2010/0096416 A1 | 4/2010 | Painchaud et al. |
| 2011/0125111 A1 | 5/2011 | Chibret et al. |
| 2012/0067926 A1 | 3/2012 | Ishikawa et al. |
| 2012/0312840 A1 | 12/2012 | Hasegawa et al. |

* cited by examiner

NOZZLE AND CONTAINER FOR DISPENSING A LIQUID

FIELD OF THE INVENTION

This invention concerns the field of liquid dispensing, especially in the form of drops, in the pharmaceutical field, for example ophthalmic liquid, but also in any other field such as in the cosmetics or food sectors.

In particular, the invention concerns the dispensing of preservative-free liquid, in the form of drops.

BACKGROUND OF THE INVENTION

The current trend is to supply products, especially ophthalmic products, that do not contain preservatives. The sterility of the product must thus be guaranteed throughout the use of the bottle containing the liquid to be delivered.

From document WO92/01625, various devices are known that enable the delivery of drops of product contained in a reservoir and which prevent contamination of the liquid remaining in the bottle.

According to one example, such a liquid dispensing device includes a reservoir and a dispensing tip mounted on the reservoir, provided with a liquid dispensing opening. The dispensing tip comprises a valve which allows liquid to exit but prevents it from entering, which limits the risk of introducing bacteria or contaminating substances into the bottle. Such a valve is also referred to as a "check valve". The user applies pressure to the reservoir causing it to become deformed and, under the effect of pressure, a drop passes through the valve and forms on the surface of the dispensing opening. The valve closes once the desired quantity of drops is delivered.

A problem with this type of device is that although the valve closes, a small residual quantity of product remains on the surface of the tip after the dosed drop or drops are delivered and this small residual quantity of product may be the point from which contamination may spread into the bottle.

This propagation is a surprising phenomena which contradicts the operating principle of the valve, but which the inventors behind this invention have highlighted.

A posteriori, the inventors explain this phenomenon by the fact that the position of the boundary between the inside and the outside of the bottle is not fixed on the valve, but moves, over the course of successive openings and closings, around an average position. As a result, in the areas surrounding this boundary, there are adjacent areas that are sometimes inside or outside the bottle, i.e. outside the boundary, and sometimes included within this boundary.

After several opening-closing manoeuvres, the contaminations can find a path of slow migration via these adjacent zones, first from the outside of the bottle toward the boundary, then from the boundary toward the inside of the bottle.

SUMMARY OF THE INVENTION

This invention aims to remedy this drawback by proposing a liquid dispensing valve that ensures that contamination does not spread inside the bottle.

In this respect, an object of the invention is a liquid dispensing tip for mounting on a container, said tip comprising a valve which, in rest position, seals off the container by separating an upstream volume from a downstream volume, said valve being able to withstand opening manoeuvres by elastic deformation, said valve comprising at least two elements that are mobile in relation to each other, each mobile element including a bearing zone against the other mobile element, arranged so that, when the valve is in rest position, the bearing zones of the mobile elements bear at least partially against one another forming a surface barrier separating the upstream volume from the downstream volume, at least one of the two mobile elements being such that after one or several opening manoeuvres, said surface barrier no longer covers the same part of the bearing zone of at least one of the mobile elements, characterised in that at least one of the mobile elements bears an anti-microbial material on or in the immediate proximity of a part of its bearing zone which is covered by the surface barrier, and in that the entire surface of the dispensing tip in contact with the upstream volume when the valve is in rest position is free of anti-microbial material.

Within the meaning of the invention, "in the immediate proximity" means that the distance between the bearing zone and the anti-microbial material is less than 3 mm, and preferably, less than 1 mm. It is important that this distance is small in order to prevent proliferation or displacement of bacteria into the downstream volume. It is known that bacteria can reproduce very rapidly in favourable conditions. In addition, certain bacteria are able to move at surprising speeds, for example 2 mm per minute, hence the importance of preventing the presence of bacteria in the immediate vicinity of the valve in order to prevent them from entering the container.

According to other features of the invention, which may be considered alone or in combination:
- the anti-bacterial material is present in the form of a layer which covers at least partially the bearing zone of one of the mobile elements,
- the anti-bacterial material is present in the form of an excess thickness protruding from the bearing zone of one of the mobile elements,
- the excess thickness substantially occupies the thickness of an opening of the valve,
- one of the mobile elements has undergone an anti-bacterial treatment on part of its thickness,
- one of the mobile elements is co-moulded with anti-bacterial material,
- one of the mobile elements comprises an insert,
- the insert is made from bulk anti-bacterial material,
- the insert is coated externally by a layer of anti-bacterial material,
- only the face of the insert turned toward the outside is coated with a layer of anti-bacterial material,
- the insert is flush with the bearing zone of the mobile element,
- the insert protrudes from the bearing zone of the mobile element so as to form a pin passing through an opening of the valve,
- one of the mobile elements is coated, on a face bearing the anti-bacterial material, with a layer of non anti-bacterial insulating material in its parts located upstream from the valve,
- one of the mobile elements is a sealing pin substantially cylindrical in shape and the other mobile element is a membrane comprising a cylindrical part capping the pin and leaving an annular gap around it forming a flow channel, the surface barrier having a substantially annular shape.

Another object of the invention is a liquid dispensing container comprising a reservoir on which a dispensing tip is mounted as described above, and notably a container for dispensing ophthalmic liquid.

BRIEF DESCRIPTION OF THE DRAWINGS

The invention shall be better understood upon reading the following description, which does not limit the scope of the invention in any way and is provided only as an example with reference to the following drawings in which.

DETAILED DESCRIPTION OF THE INVENTION

Figure 1:
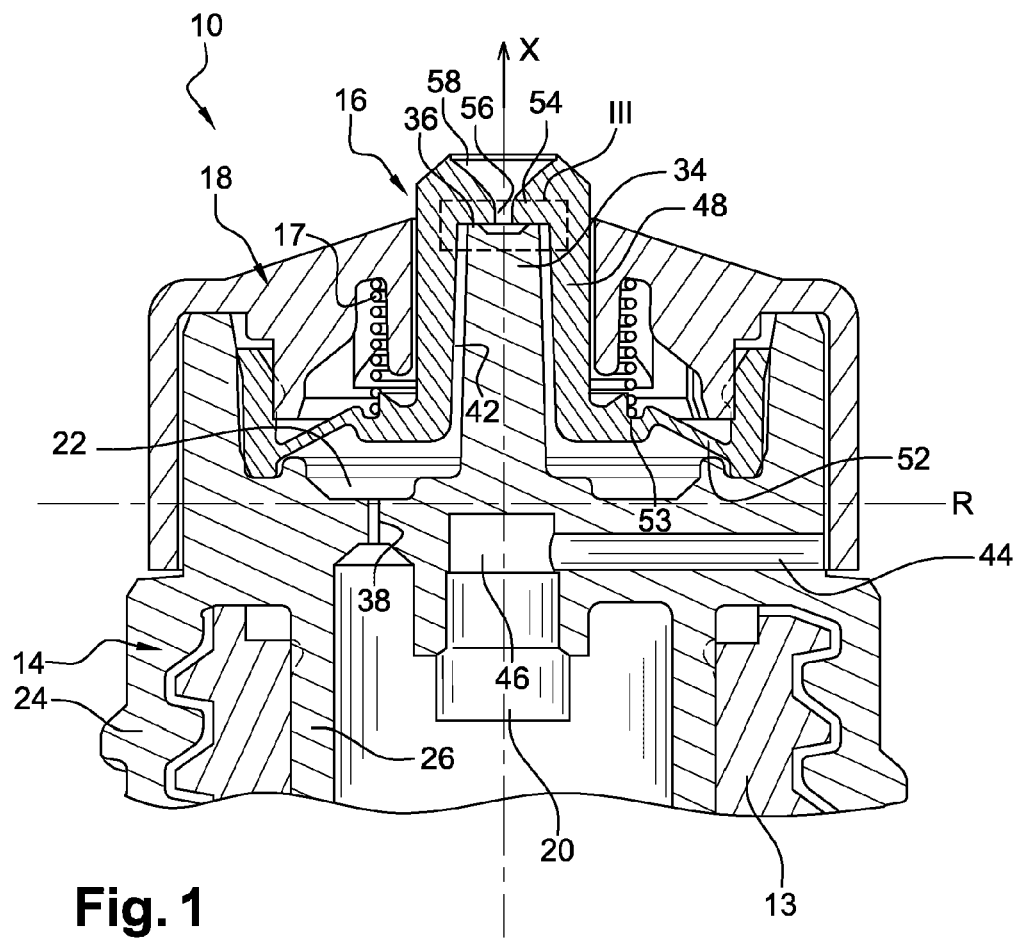
FIG. 1 is a cross-sectional view of a device according to the invention.
Figures 2A, 2B, 2C, 2D:
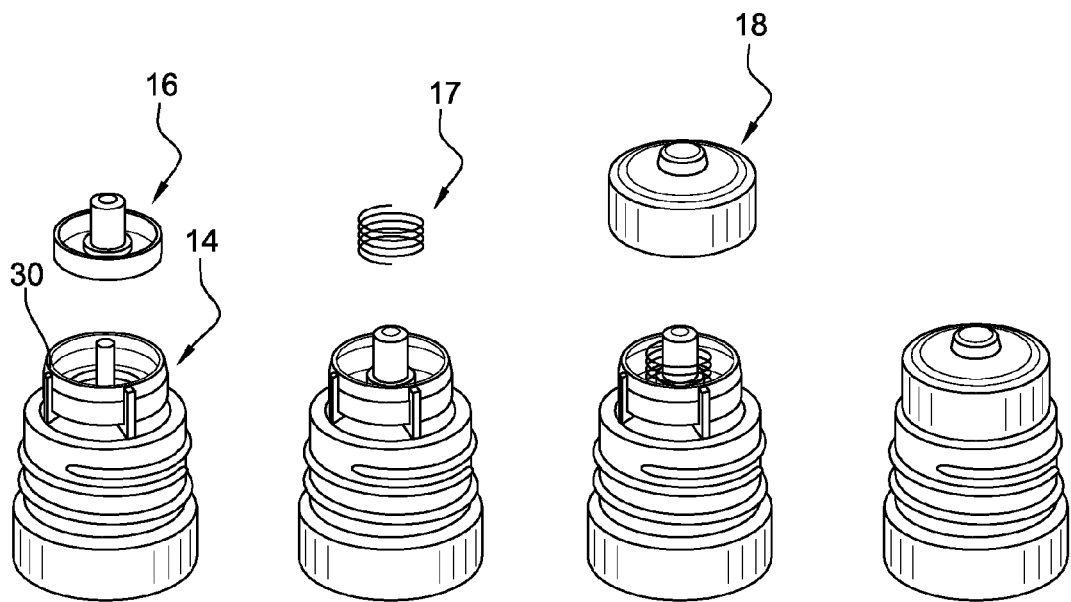
FIGS. 2a to 2d represent, individually and in perspective, various components of the device.

FIG. 1 shows a tip 10 for dispensing liquid in the form of a drop, for screw mounting onto the neck 13 of a reservoir (of which only the neck 13 is visible in FIG. 1). This reservoir is a storage reservoir for a liquid, for example pharmaceutical liquid such as ophthalmic liquid. As already known, the reservoir is deformable and can be compressed to initiate dispensing of the liquid. More precisely, the liquid is dispensed by pressure, applied by a user, on the body of the reservoir, the latter having a certain elasticity to enable it to return to its initial shape after the pressure is released.

In this example, the dispensing tip 10 comprises a support 14, a membrane 16 equipped with a dispensing opening 58, a spring 17, an outer envelope 18, a flow channel 38 for passing liquid from the reservoir toward the dispensing tip 58 and a channel 44 for allowing air into the reservoir, channel 44 which is plugged by an air-permeable sterilising component 46 that is not described here.

In this example, the support 14 comprises a fastening part 24 to the reservoir, placed at the proximal end of the support 14. The part 24 comprises an external skirt including a screw thread enabling it to be screwed onto the neck 13 of the reservoir. The fastening part 24 also includes a tubular-shaped internal skirt 26, enabling it to ensure the seal between the reservoir and the dispensing tip 10.

Furthermore, the support 14 includes a central sealing pin 34, essentially cylindrical in shape and extending in the distal direction, opposite to the internal skirt 26. The pin 34 comprises, on its distal end, a bearing zone 36 of the pin 34 against the membrane 16 which blocks the flow of liquid in blocking configuration. In this example, the bearing zone 36 has an annular rib shape.

In this example, the support 14 also comprises a housing 20 forming a cavity that is essentially cylindrical in shape, this cavity opening to the reservoir at its proximal end and opening to the liquid flow channel 38 at its distal end, provide for in the support 14 and extending in the longitudinal direction of the device, corresponding to the direction of ejection. Channel 38 opens to an intermediate cavity 22, itself opening to a second liquid flow channel 42.

The membrane 16 is part a revolving part with special geometry, whose non-relevant details, with regard to the invention, will not be described here. The membrane 16 includes a cylindrical part 48 capping the pin 34 leaving an annular gap around it forming the aforementioned second channel 42 and, at the distal end of this cylindrical part 48, a washer 54 provided with a central opening 56 forming the small base of a cone frustum open toward the outside, whose large base corresponds to the dispensing opening 58 of the membrane. The washer 54 is formed in a single piece with the cylindrical part 48. Its internal face 55 rests on the bearing zone 36 of the pin, owing to the action of the spring 17 which pushes the cylindrical part 48 downward while exerting pressure on a seat 53 formed at the base of the cylindrical part 48. Owing to a flexible zone 52, the membrane 16 may deform in order to allow its cylindrical part 48 to slide axially around the pin 34. The internal face 55 forms a bearing zone of the membrane 16 against the pin 36. Subject to deformation of the membrane 16, the bearing zone 55 of the washer 54 may lift off the bearing zone 36 of the pin and open a passage between the inside and the outside of the device. This thus how product dispensing is rendered possible: pressure exerted on the walls of the bottle cause the pressure of the liquid to increase, which pushes on the membrane 16 and moves apart the membranes 16 and the pin 34 and allows the liquid to reach the dispensing opening 58. In normal conditions of use of the device, no circumstance other than that of overpressure in the liquid is foreseen so that the washer 54 lifts off the bearing zone 36. Membrane 16 and pin 34 thus form two elements, that are mobile in relation to one another, of a valve separating an upstream volume from a downstream volume, a valve which prevents the liquid which left the inside of the device, i.e. flowing from the upstream volume to the downstream volume, from returning in the device.

Figure 3:
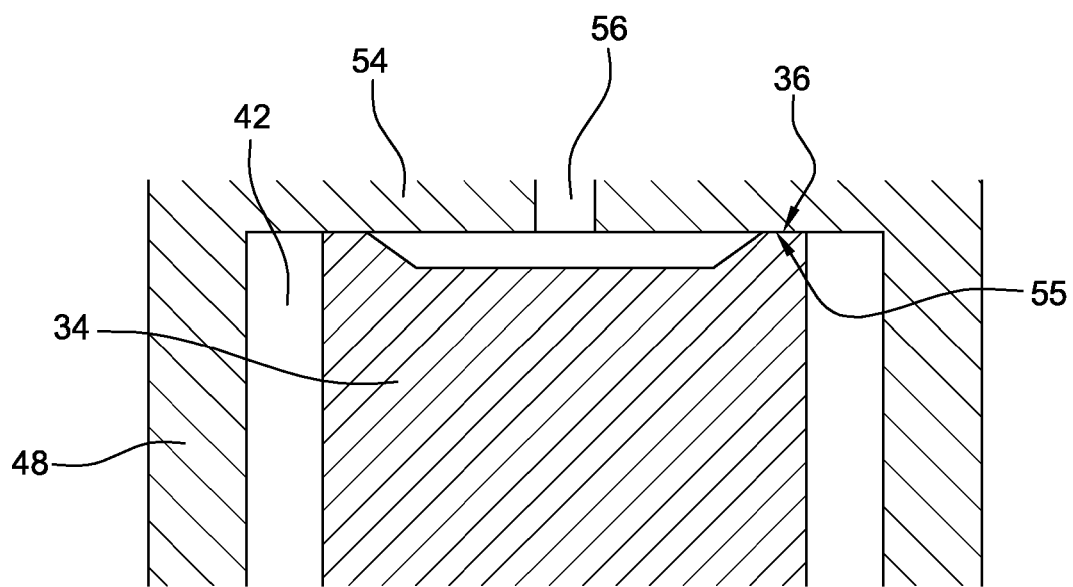
FIG. 3 is a cross-sectional view, in a larger scale, of region III of FIG. 1.
Figure 4:
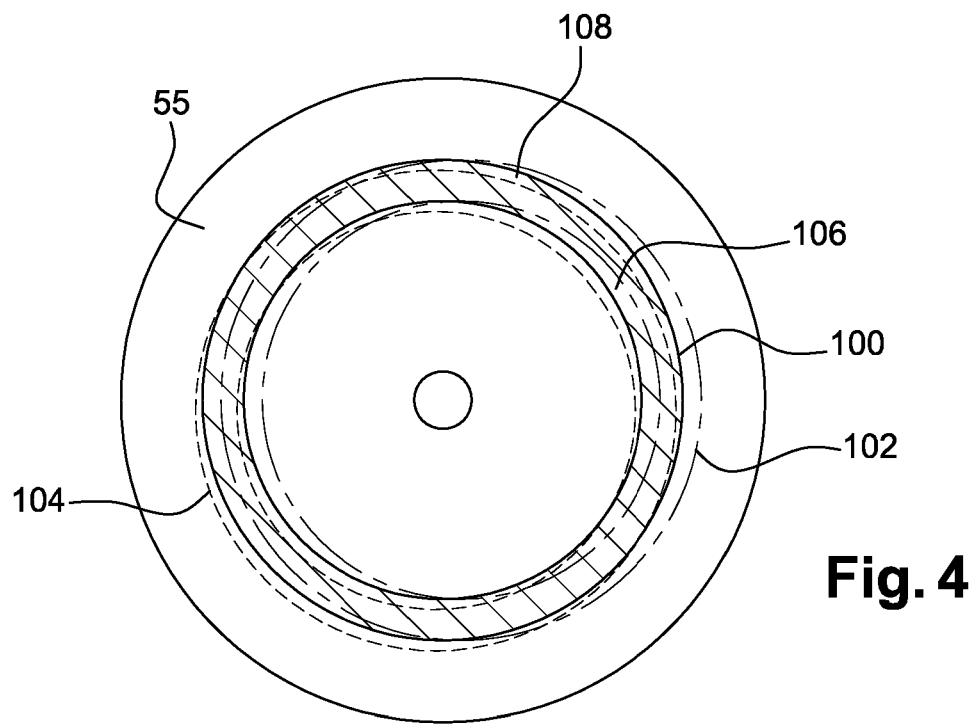
FIG. 4 is a bottom view of the washer of FIG. 3, FIGS. 5 to 28 are views similar to FIG. 3, illustrating alternative embodiments of the invention.

This valve is represented in a larger scale in FIGS. 3 and 4.

It can be seen that, when the valve is in rest position, thus closed, the separation between the upstream volume and the downstream volume is ensured by a surface barrier extending, on the bearing zone 36 side, over this entire zone, and, on the washer 54 side, over the part of the internal face 55 that is in contact with the bearing zone 36.

But as the centering of the washer 54 in relation to the bearing zone 36 is ensured only the elasticity of the membrane 16, by dint of successive openings and closings, the fatigue of the membrane 16 or any other disturbance of the equilibrium of the forces within the membrane may result in the washer 54 not returning exactly to the same position on the bearing zone 36. Thus, at micrometric or less scale, although in any case greater than the magnitude of the bacteria likely to contaminate the liquid, the blocking surface barrier moves, at least on the internal face side 55 of the washer 54, around an average theoretical position and leaves, in the area around these edges, adjoining zones which are sometimes inside or outside the dispensing device, i.e. excluded from the surface barrier, sometimes included in this surface barrier.

In FIG. 4, the surface barrier, which corresponds to the surface on which the bearing zone 55 and the bearing zone 36 touch, is shown by a shaded ring 100 in a first closed position of the valve. After a few openings and closings, this ring takes another position 102, drawn with short and long dashes. Then, after another a few openings and closings, the ring takes still another position 104, drawn in dotted lines.

It can be seen that if a bacterium was lodged in a location 106 of the bearing zone 55 located in the immediate vicinity of the surface barrier in position 102, i.e. in the downstream volume, when the barrier would take position 100, the bacterium would no longer be in the downstream volume of the valve, but in the surface barrier, where it could migrate closer and closer, each time the valve is opened, until it reached location 108 located in the surface barrier in position 100, but in the upstream volume if the surface barrier assumes the position 104. The bacterium would have thus reached the inside of the container and could contaminate all the liquid that it contains.

The bearing zone 36 is coated with a layer 110 of anti-bacterial material, silver ion-based in this example, which prevents any proliferation of bacteria in the immediate vicinity of the surface barrier. Thus, even if a bacterium manages to attach itself to the location 106 when the surface barrier is in position 102, it will not be able to survive if it is located, by displacement of the surface barrier in position 100 or 104, in contact with the anti-bacterial layer of the bearing zone 36 in position 104. The anti-bacterial layer thus efficiently fulfils its function to prevent the influx into the upstream volume of contaminants for the liquid present in the reservoir.

The anti-bacterial layer is not present on any surface of the membrane 16 or support 14 in contact with the liquid upstream from the valve, so that no chemical reaction detrimental to the liquid occurs in this upstream volume.

Other alternative embodiments procuring the same protective effects are represented in FIGS. 5 to 28. In these figures, the pin 34' does not have an annular rib but includes a flat upper face including the bearing zone 36'. The surface barrier is still a ring, this time extending from the peripheral edge of the pin to the edge of the opening 56' of the washer 54'. The cone frustum of the previous figures, between openings 56 and 58, is replaced by a semi-spherical portion joining the openings 56' and 58', but still defines a dead volume of liquid downstream from the valve. For clarity reasons, the reference numbers 36', 54', 56', 58' were not indicated on FIGS. 6 to 28, on which it is easy to recognise the corresponding elements that are identical.

Figures 5, 6, 7:
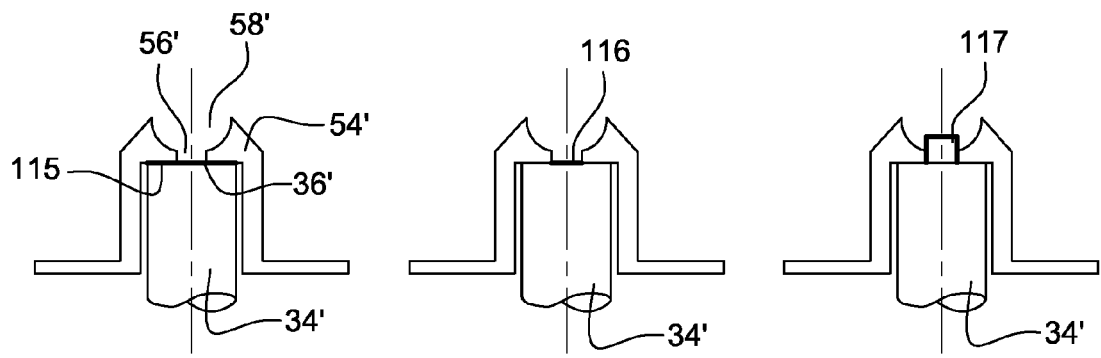

In FIG. 5, the anti-bacterial layer 115 covers the entire upper face of the pin 34'. It may thus act against bacteria that may have slid into the surface barrier and against bacteria developing in the residual volume of the liquid present in the downstream dead volume, near the opening 56'.

In FIG. 6, the anti-bacterial layer 116 covers the part of the upper face of the pin 34' located opposite the opening 56'.

In FIG. 7, the anti-bacterial layer 117 forms an excess thickness protruding from the upper face of the pin 34' and occupies the entire thickness of the opening 56'.

Figures 8, 9, 10:
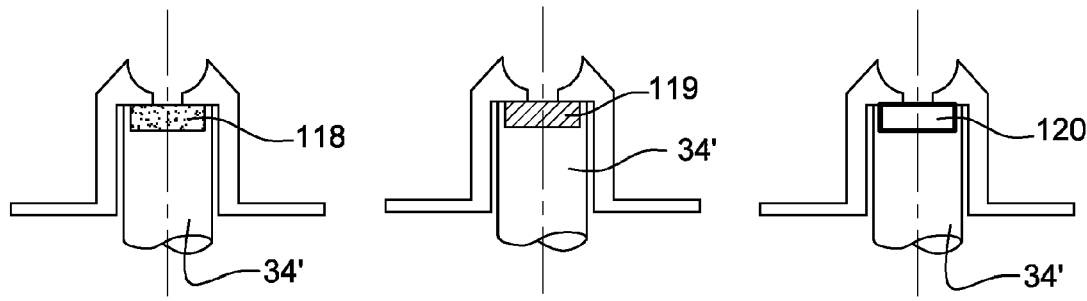

In FIG. 8, the pin 34' has undergone anti-bacterial treatment over a part 118 of its thickness, in a central region excluding the edges of its upper face.

In FIG. 9, the pin 34' is co-moulded with anti-bacterial material, or comprises an insert 119 made of bulk anti-bacterial material, present in a central region of its upper face excluding the edges of this face and flush with said face.

In FIG. 10, the pin 34' comprises an insert 120 coated by a anti-bacterial material layer on the outside, lodged in a central region of its upper face excluding the edges of this face.

Figures 11, 12, 13:
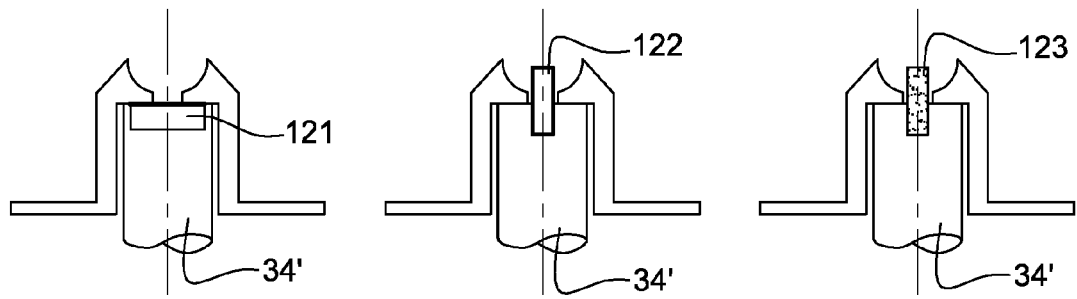

In FIG. 11, the insert 121 is nearly identical but is coated only on its face turned toward the outside.

In FIG. 12, the pin 34' comprises a insert 122 made of bulk anti-bacterial material, present in a central region of its upper face opposite the opening 56' and protruding from said face so as to form a pin passing through the opening 56'.

In FIG. 13, the pin 34' comprises an insert 123 whose shape is identical to the previous insert but co-moulded with the pin 34'.

Figures 14, 15, 16:
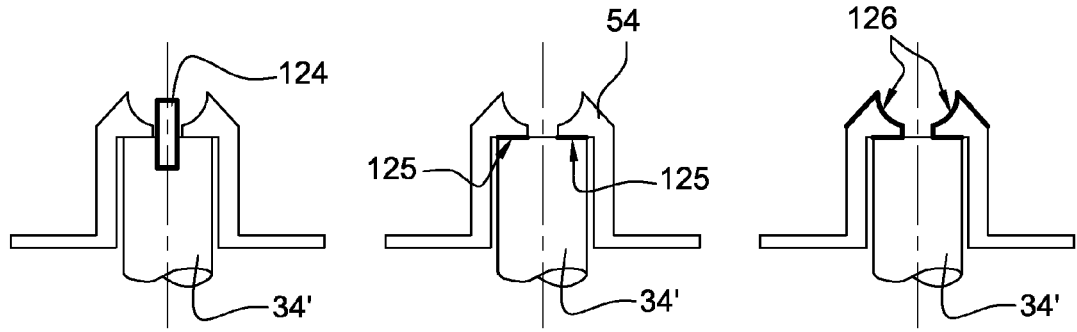

In FIG. 14, the pin 34' comprises an insert 124 nearly identical to that of FIG. 12 but only coated with anti-bacterial material on its external faces.

In FIG. 15, the anti-bacterial layer 125 is present on the washer 54, in its part opposite the pin 34', excluding the part of the washer opposite the peripheral edge of the pin 34'.

In FIG. 16, the anti-bacterial layer 126 extends, in addition to that of FIG. 15, onto the edge of the semi-spherical cavity and even beyond the opening 58'.

Figure 17:
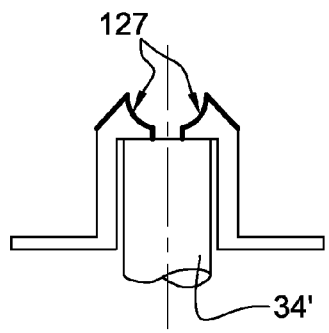

In FIG. 17, the anti-bacterial layer 127 extends only on the edge of the semi-spherical cavity and beyond the opening 58'.

Figure 18:
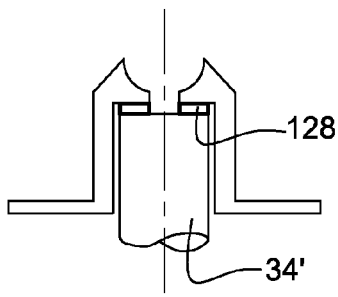

In FIG. 18, the anti-bacterial layer 128 forms an excess thickness protruding from the washer, excluding opening 58', opposite the bearing zone of the pin 34' except for the peripheral edge of the latter.

Figure 19:
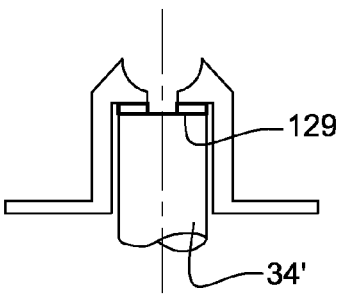

In FIG. 19, the anti-bacterial layer 129 has the same shape as previously but is co-moulded with the washer or results from an anti-bacterial treatment of the washer on a part of its thickness, except for its part opposite the peripheral edge of the pin 34'.

Figure 20:
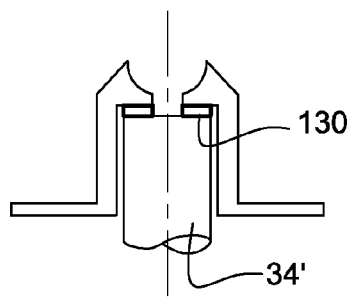

In FIG. 20, the anti-bacterial layer 130 has the same shape as previously but is an insert coated externally by a layer of anti-bacterial material.

Figure 21:
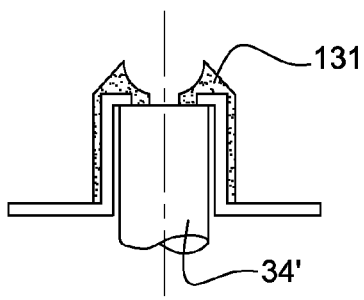

In FIG. 21, the anti-bacterial layer 131 is a solid double thickness portion of the membrane, giving it its external shape and covering its part capping the pin 34'.

Figure 22:
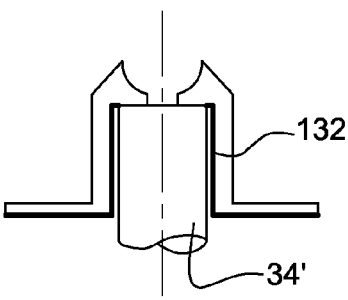

In FIG. 22, the membrane is integrally coated with a layer of anti-bacterial material and this layer is itself coated with an insulation layer 132 made of non anti-bacterial material in its parts located upstream from the valve, apart from the external edge of the pin 34'.

Figure 23:
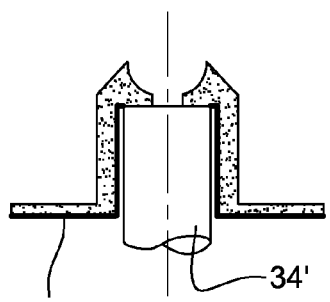

In FIG. 23, the membrane consists largely of anti-bacterial material and is covered with an insulation layer 133 made of non anti-bacterial material in its parts located upstream from the valve, apart from the external edge of the pin 34'.

Figure 24:
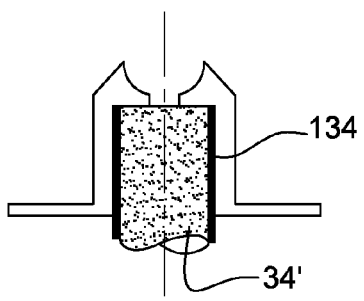

In FIG. 24, the pin 34' consists of anti-bacterial material and is covered by an insulation layer 134 made of non anti-bacterial material in its parts located upstream from the valve.

Figure 25:
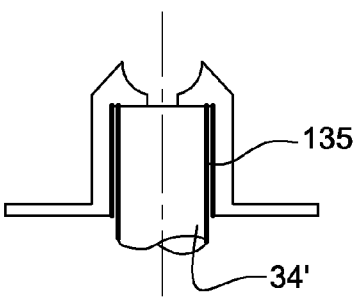

In FIG. 25, the pin 34' is coated by an anti-bacterial material and is itself coated by an insulation layer 135 made of non anti-bacterial material in its parts located upstream from the valve.

All the possible combinations of these variants are possible, as long as they fall within the definition of the invention.

Figure 26:
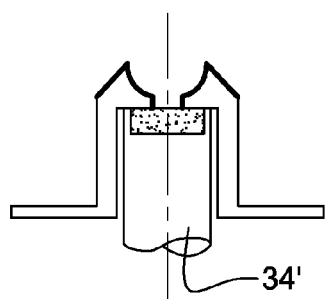
Figure 27:
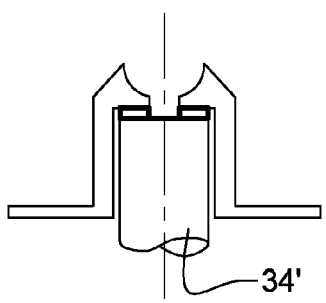
Figure 28:
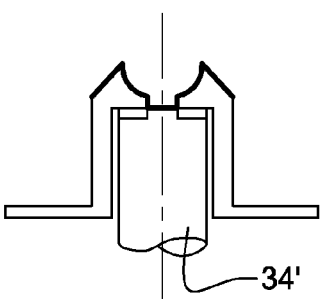

For example, the characteristics of the alternative embodiments of FIGS. 8 and 17 were combined in FIG. 26. In FIG. 27, the characteristics of the alternative embodiments of FIGS. 5 and 18 were combined and, in FIG. 28, the characteristics of the alternative embodiments of FIGS. 6 and 17 were combined.

It is understood that the examples of embodiment described do not limit the scope of the invention and that other variants and combinations of variants are possible.

What is claimed is:

1. A liquid dispensing tip for mounting on a container, said tip comprising a valve which, in rest position, seals off the container by separating an upstream volume from a downstream volume, said valve being able to withstand opening manoeuvres by elastic deformation, said valve comprising a support and a membrane that is mobile in relation to the support, each of the support and the membrane including a bearing zone against each other, arranged so that, when the valve is in rest position, the bearing zones of the support and the membrane bear at least partially against one another forming a surface barrier separating the upstream volume from the downstream volume, at least one of the support or the membrane being such that after one or several opening manoeuvres, said surface barrier no longer covers the same part of the bearing zone of at least one of the support or the membrane, said tip further comprising an antimicrobial material on the membrane, the anti-microbial material being only on the bearing zone of the membrane or on the membrane in the immediate proximity of its bearing zone, such that the entire surface of the dispensing tip in contact with the upstream volume when the valve is in rest position is free of anti-microbial material,
  wherein the membrane comprises an inner portion and an outer portion, wherein the outer portion includes the anti-microbial material and the inner portion is free of antimicrobial material, the outer portion surrounding a distal end of the inner portion and contacting the support in the bearing zone.

2. The tip according to claim 1, wherein the outer portion of the membrane including the anti-microbial material forms a semi-spherical cavity with an opening.

3. The tip according to claim 1, wherein at least one of the membrane or the support is co-moulded with antimicrobial material.

4. The tip according to claim 1, wherein at least one of the membrane or the support has undergone an antimicrobial treatment on part of its thickness.

5. The tip according to claim 1, wherein the support includes a part, including antimicrobial material, located only in a central region of the support excluding edges of an upper face of the support.

6. The tip according to claim 1, wherein the tip further comprising an anti-microbial material on the support, wherein the support is a sealing pin substantially cylindrical in shape and the membrane comprises a cylindrical part capping the pin and leaving an annular gap around it forming a flow channel, and wherein the surface barrier has a substantially annular shape, the anti-microbial material being a layer present on an upper face of the support.

7. A liquid dispensing tip for mounting on a container, said tip comprising a valve which, in rest position, seals off the container by separating an upstream volume from a downstream volume, said valve being able to withstand opening manoeuvres by elastic deformation, said valve comprising a support and a membrane that is mobile in relation to the support, each of the support and the membrane including a bearing zone against each other, arranged so that, when the valve is in rest position, the bearing zones of the support and the membrane bear at least partially against one another forming a surface barrier separating the upstream volume from the downstream volume, at least one of the support or the membrane being such that after one or several opening manoeuvres, said surface barrier no longer covers the same part of the bearing zone of at least one of the support or the membrane, said tip further comprising an anti-microbial material on at least one of the support or the membrane, the anti-microbial material being only on the bearing zone of the at least one of the support or the membrane, or on the at least one of the support or the membrane in the immediate proximity of its bearing zone, such that the entire surface of the dispensing tip in contact with the upstream volume when the valve is in rest position is free of anti-microbial material,
  wherein the membrane comprises a semi-spherical cavity and an anti-microbial layer extending on an edge of the semi-spherical cavity.

8. The tip according to claim 7, wherein the membrane comprises a washer provided with a central opening, the anti-microbial layer being present on the washer, in its part opposite the support, excluding the part of the washer opposite a peripheral edge of the support.

9. The tip according to claim 7, wherein the anti-bacterial layer extends on the edge of the semi-spherical cavity and beyond the opening.

10. The tip according to claim 7, wherein at least one of the membrane or the support is co-moulded with antimicrobial material.

11. The tip according to claim 7, wherein at least one of the membrane or the support has undergone an antimicrobial treatment on part of its thickness.

12. The tip according to claim 7, wherein the support includes a part, including antimicrobial material, located only in a central region of the support excluding edges of an upper face of the support.

13. The tip according to claim 7, wherein the tip further comprising an anti-microbial material on the support, wherein the support is a sealing pin substantially cylindrical in shape and the membrane comprises a cylindrical part capping the pin and leaving an annular gap around it forming a flow channel, and wherein the surface barrier has a substantially annular shape, the anti-microbial material being a layer present on an upper face of the support.

14. A liquid dispensing tip for mounting on a container, said tip comprising a valve which, in rest position, seals off the container by separating an upstream volume from a downstream volume, said valve being able to withstand opening manoeuvres by elastic deformation, said valve comprising a support and a membrane that is mobile in relation to the support, each of the support and the membrane including a bearing zone against each other, arranged so that, when the valve is in rest position, the bearing zones of the support and the membrane bear at least partially against one another forming a surface barrier separating the upstream volume from the downstream volume, at least one of the support or the membrane being such that after one or several opening manoeuvres, said surface barrier no longer covers the same part of the bearing zone of at least one of the support or the membrane, said tip further comprising an anti-microbial material on at least one of the support or the membrane, the anti-microbial material being only on the bearing zone of the at least one of the support or the membrane or on the at least one of the support or the membrane in the immediate proximity of its bearing zone, such that the entire surface of the dispensing tip in contact with the upstream volume when the valve is in rest position is free of anti-microbial material,
  wherein the anti-microbial material is present in the form of an excess thickness protruding from the bearing zone of one of the support or the membrane.

15. The tip according to claim 14, wherein the excess thickness substantially occupies the thickness of an opening of the valve.

16. The tip according to claim 14, at least one of membrane or the support is co-moulded with material.

17. The tip according to claim 14, wherein at least one of the membrane or the support has undergone an antimicrobial treatment on part of its thickness.

18. The tip according to claim 14, wherein the support includes a part, including antimicrobial material, located only in a central region of the support excluding edges of an upper face of the support.

19. The tip according to claim 14, wherein the tip further comprising an anti-microbial material on the support, wherein the support is a sealing pin substantially cylindrical in shape and the membrane comprises a cylindrical part capping the pin and leaving an annular gap around it forming a flow channel, and wherein the surface barrier has a substantially annular shape, the anti-microbial material being a layer present on an upper face of the support.

* * * * *

UNITED STATES PATENT AND TRADEMARK OFFICE
CERTIFICATE OF CORRECTION

PATENT NO. : 9,579,671 B2  
APPLICATION NO. : 14/984247  
DATED : February 28, 2017  
INVENTOR(S) : Thierry Decock et al.

Page 1 of 1

It is certified that error appears in the above-identified patent and that said Letters Patent is hereby corrected as shown below:

On the Title Page

Item (71) and (72):
"Thierry Decock, Lyons (FR)" should be changed to --Thierry Decock, Lyon (FR)--

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*